United States Patent
Young et al.

(10) Patent No.: US 9,655,601 B2
(45) Date of Patent: May 23, 2017

(54) ERGONOMIC HANDPIECE FOR LAPAROSCOPIC AND OPEN SURGERY

(71) Applicant: SRA DEVELOPMENTS LIMITED, South Devon (GB)

(72) Inventors: Michael John Radley Young, South Devon (GB); Christopher John Leaver, South Devon (GB); Nicholas Charles Wright, South Devon (GB); Peter James Manley, South Devon (GB)

(73) Assignee: SRA DEVELOPMENTS LIMITED, South Devon (GB)

( * ) Notice: Subject to any disclaimer, the term of this patent is extended or adjusted under 35 U.S.C. 154(b) by 0 days.

(21) Appl. No.: 15/050,893

(22) Filed: Feb. 23, 2016

(65) Prior Publication Data

US 2016/0242753 A1 Aug. 25, 2016

Related U.S. Application Data

(63) Continuation of application No. 13/279,480, filed on Oct. 24, 2011, now abandoned.

(30) Foreign Application Priority Data

Oct. 23, 2010 (GB) .................................. 1017968.7
Nov. 22, 2010 (GB) .................................. 1019794.5

(Continued)

(51) Int. Cl.
*A61B 18/04* (2006.01)
*A61B 17/00* (2006.01)
(Continued)

(52) U.S. Cl.
CPC ........ *A61B 17/00234* (2013.01); *A61B 17/29* (2013.01); *A61B 17/320092* (2013.01);
(Continued)

(58) Field of Classification Search
CPC ............ A61B 17/29; A61B 17/320092; A61B 2019/4857; A61B 2017/00398; A61B 2017/320096; A61B 2017/0017; A61B 2017/2929

(56) References Cited

U.S. PATENT DOCUMENTS 3,862,630 A   1/1975   Balamuth
4,841,189 A   6/1989   Cooper et al.
(Continued)

OTHER PUBLICATIONS

International Search Report for PCT/GB2011/001526, dated Feb. 9, 2012.

*Primary Examiner* — Rex R Holmes
(74) *Attorney, Agent, or Firm* — Heslin Rothenberg Farley & Mesiti P.C.

(57) ABSTRACT

A surgical tool having an elongate shaft, with a directional operative element at its distal end, is provided with a mechanism to rotate the shaft and the operative element about a longitudinal axis shaft. This allows the operative element to be aligned with an element of tissue without excessive hand movement by the user. In a preferred version, the mechanism is electrically powered and is regulated to produce smooth, controlled, accurate motion between selected rotational positions. The mechanism may include a linear magnetic motor drive to move a drive element longitudinally along the tool. This drive element is engaged with a helical formation on a drive shaft, such that longitudinal motion of the drive element is converted to rotational motion of the drive shaft, and of the shaft and operative element, to which the shaft is mounted.

22 Claims, 13 Drawing Sheets

(30) Foreign Application Priority Data

Dec. 6, 2010 (GB) .................................. 1020672.0
Feb. 4, 2011 (GB) .................................. 1102034.4

(51) Int. Cl.
*A61B 17/29* (2006.01)
*A61B 17/32* (2006.01)
*A61B 90/00* (2016.01)

(52) U.S. Cl.
CPC .............. *A61B 18/04* (2013.01); *A61B 90/08* (2016.02); *A61B 2017/00017* (2013.01); *A61B 2017/00398* (2013.01); *A61B 2017/2929* (2013.01); *A61B 2017/320096* (2013.01); *A61B 2090/0811* (2016.02)

(58) Field of Classification Search
USPC ... 606/32, 34, 37, 38, 41, 42, 167–171, 205, 606/206; 600/437, 439, 442
See application file for complete search history.

(56) References Cited

U.S. PATENT DOCUMENTS

| | | |
|---|---|---|
| 5,322,055 A | 6/1994 | Davison et al. |
| 5,447,513 A | 9/1995 | Davison et al. |
| 5,938,633 A | 8/1999 | Beaupre |
| 6,024,750 A | 2/2000 | Mastri et al. |
| 6,056,735 A | 5/2000 | Okada et al. |
| 6,063,050 A | 5/2000 | Manna et al. |
| 6,245,084 B1 | 6/2001 | Mark et al. |
| 6,352,532 B1 | 3/2002 | Kramer et al. |
| 6,468,286 B2 | 10/2002 | Mastri et al. |
| 6,682,544 B2 | 1/2004 | Mastri et al. |
| 6,887,252 B1 | 5/2005 | Okada et al. |
| 7,963,433 B2 * | 6/2011 | Whitman et al. .......... 227/178.1 |
| 8,419,759 B2 * | 4/2013 | Dietz ............................ 606/169 |
| 2002/0019646 A1 | 2/2002 | Mastri et al. |
| 2010/0192568 A1 | 8/2010 | Peacock |
| 2010/0193567 A1 | 8/2010 | Scheib et al. |

* cited by examiner

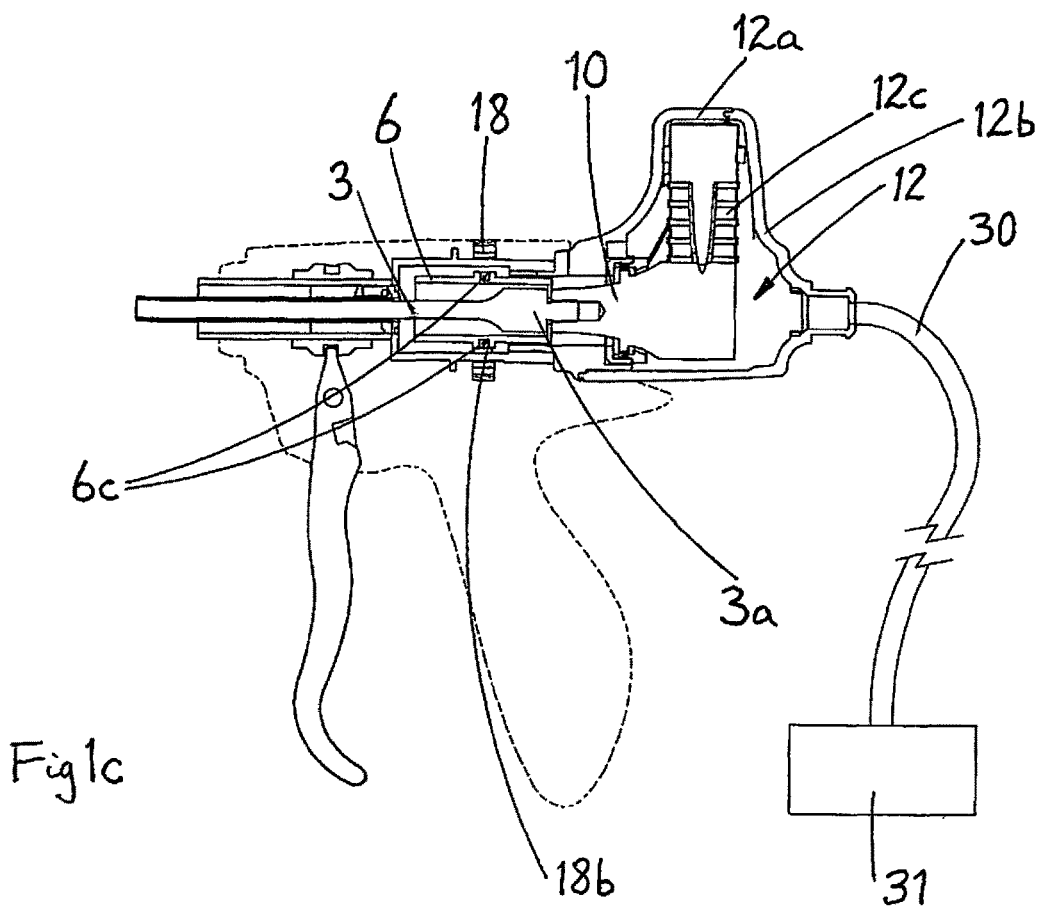
Fig 1c
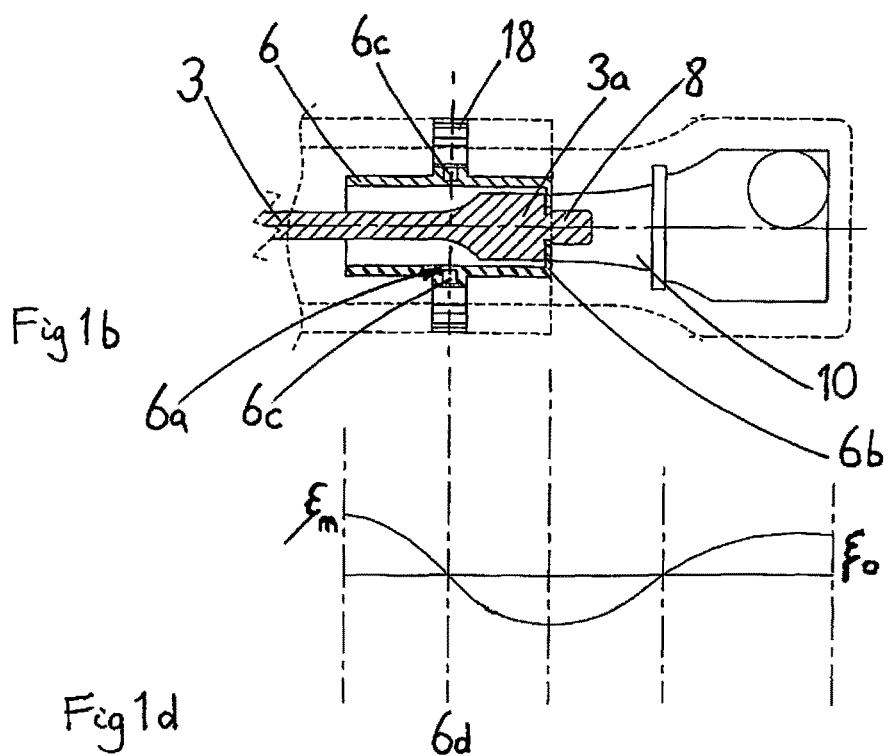
Fig 1b
Fig 1d

ERGONOMIC HANDPIECE FOR LAPAROSCOPIC AND OPEN SURGERY

CROSS REFERENCE TO RELATED APPLICATIONS

This application is a continuation of Ser. No. 13/279,480 filed on Oct. 24, 2011, and claims priority of United Kingdom applications GB1017968.7 filed on Oct. 23, 2010, GB1019794.5 filed on Nov. 22, 2010, GB1020672.0 filed on Dec. 6, 2010, and GB1102034.4 filed on Feb. 4, 2011, the entire contents of all of these applications being hereby incorporated by reference herein.

BACKGROUND ART

The present invention relates to a surgical tool, and to a mechanism for its operation. More particularly, but not exclusively, it relates to such a tool having improved ease of manual control.

Over the past 20 years, much effort has been applied to the development of specialised surgical instruments which allow complex procedures to be performed with predictable outcome. (For example, see U.S. Pat. No. 6,887,252; U.S. Pat. No. 6,056,735; U.S. Pat. No. 6,063,050 and U.S. Pat. No. 6,468,286). Many of these devices are designed to manipulate and dissect biological tissues. These devices may be manually operated or alternatively may incorporate a powered element designed to deliver an enhanced tissue cutting performance with significant haemostasis: see for example U.S. Pat. No. 5,938,633; U.S. Pat. No. 5,322,055 and U.S. Pat. No. 6,352,532. Both ultrasound and RF electrical currents are commonly used to energise such instruments. The above instruments also embody ergonomic features associated with basic hand instruments providing core surgical needs.

A review of modern clinical trends related to the field of general surgery indicates an expectation on the part of specialists in minimal invasive surgery that any instruments offered in the future will incorporate significantly enhanced handpiece designs, in order to enable the surgeon successfully to undertake long, intricate procedures without experiencing fatigue, which could compromise the surgical outcome.

There have been past attempts to provide relevant functionalities addressing the requirements for controlling the cutting plane orientation, combined with accurate tissue targeting. These have been limited by inadequate mechanism designs, which impose physical constraints on the surgeons' ability to operate freely. For example, mechanisms have been proposed in which the cutting plane of the surgical tool is rotated by pushing with the surgeon's fingertip. Accurate control is difficult, and even the most dextrous surgeons find that they can rotate the cutting plane in one direction but not rotate it back in the other direction.

BRIEF SUMMARY OF THE INVENTION

It is hence an aspect of the present invention to provide a surgical tool and a mechanism for a surgical tool having enhanced ergonomic features which obviate the above problems and contribute to the above surgical requirements.

In a first aspect of the invention, special attention is paid to means of controlling the orientation of a cutting/coagulating plane of a surgical tool with respect to the manually held instrument handle According to a first aspect of the present invention, there is provided a surgical tool comprising an elongate member provided adjacent its distal end with an effector defining a plane of operation, a manipulable handpiece disposed adjacent a proximal end of the elongate member, and a rotation mechanism adapted controllably to rotate the elongate member and the effector together about a longitudinal axis of the elongate member so as to align said plane of operation of the effector in a desired orientation.

Preferably, the rotation mechanism comprises a geared transmission mechanism.

Preferably, the rotation mechanism comprises a magnetic drive mechanism.

Preferably, the rotation mechanism comprises a powered rotation mechanism operatively connected to hand-operable activation member.

The hand-operable activation member may be operable by a finger of a hand holding the handpiece.

The hand-operable activation member may be operable by finger-tip pressure.

The hand-operable activation member may be operable by finger-tip contact.

Advantageously, the hand-operable activation member comprises first and second hand-operable activation members, operation of each of which produces rotation in opposite directions.

Preferably, the elongate member comprises an elongate energy transmission member, through which energy is transmissible to activate the effector.

Advantageously, the surgical tool is adapted to be activated by ultrasonic vibrations.

The elongate energy transmission member may then comprise an elongate waveguide adapted to transmit ultrasound.

The surgical tool advantageously then also comprises a source of ultrasonic vibrations.

The source of ultrasonic vibrations may comprise a source of any one of torsional mode ultrasonic vibrations, longitudinal mode ultrasonic vibrations, flexural mode ultrasonic vibrations, and a combination of any two or more of said modes of ultrasonic vibrations.

The source of ultrasonic vibrations may comprise an amplifying horn to which the energy transmission member is mounted, and which may optionally also act as a conversion horn to produce a desired vibrational mode.

The handpiece of the tool may contain an ultrasound generator operatively linked to a proximal end of the waveguide.

Alternatively, the elongate member of the surgical tool may comprise an elongate support member for a mechanically-operable or electrically-operable effector.

The elongate member may additionally or alternatively comprise an elongate optical transmission element, the effector thereof comprising a directional viewing element, such as that of a laparoscope.

Preferably, the surgical tool comprises an operating mechanism for the effector extending operatively between the handpiece and the effector.

The effector may comprise an effecting mechanism controlled by the operating mechanism to move within the plane of operation.

The effecting mechanism may comprise a clamp adapted to grasp an element of tissue.

The clamp may comprise a jaw member moveable by the operating mechanism.

The clamp may be adapted to hold an element of tissue to the effector so that the effector may act thereon.

The effector may transmit energy from the energy transmission member into tissue adjacent the effector.

Preferably, the operating mechanism comprises a sleeve extending coaxially around the elongate member.

Advantageously, the sleeve is rotatably displaceable relative to the elongate member.

Alternatively or additionally, the sleeve may be longitudinally displaceable relative to the elongate member.

In a first embodiment, the rotation mechanism comprises a permanent magnet and a selectively energisable electromagnet, so mounted that energising the electromagnet urges the permanent magnet and the electromagnet to rotate with respect to one another.

The permanent magnet may be mounted to a first one of the handpiece and the elongate member and the electromagnet may be connected to a second one of the handpiece and the elongate member.

The permanent magnet may be mounted to the handpiece and the electromagnet to the elongate member, such that energising the electromagnet causes rotation of the elongate member relative to the handpiece.

In alternative embodiments, the rotation mechanism comprises means directly to drive said rotation.

In a second embodiment, the rotation mechanism comprises a driveable first gear operatively engaged with a driven second gear.

Advantageously, the driveable first gear is mounted to the handpiece and the driven second gear is mounted to the elongate member.

The first gear may be driven by a selectively operable motor.

In a third embodiment, the rotation mechanism comprises a longitudinally displaceable first connecting element engaged with a helical second connecting element on a rotatable body.

Advantageously, the first connecting element is mounted to the handpiece and the rotatable body comprises the elongate member.

The first connecting element may comprise a pin, optionally a ball, held within a helical slot, said helical slot comprising said second connecting element.

In a fourth embodiment, the rotation mechanism acts on an energy generation means or an energy conversion means of the surgical tool, to which said elongate energy transmission member is mounted.

Preferably, part of the energy generation or conversion means also comprises part of the rotation mechanism.

In a fifth embodiment, the rotation mechanism comprises a longitudinally-displaceable driving element operatively engaged with a rotatable driven element through helically-symmetrical engagement means.

Preferably, the helically-symmetrical engagement means comprises a body protruding from a first of the driving and driven elements and received within a helically-extending groove of a second of the driving and driven elements.

Alternatively, the helically-symmetrical engagement means may comprise a helically-extending rib protruding from a first of the driving and driven elements and received within a slot of a second of the driving and driven elements.

The protruding body preferably comprises a ball, optionally held freely rotatably to said first of the driving and driven elements.

Advantageously, the protruding body is mounted to the driving element and the helically-extending groove is located on the driven element.

Preferably, the surgical tool comprises a linear drive adapted controllably to displace the driving element.

The linear drive may comprise a linear electromagnetic motor.

The linear electromagnetic motor may comprise an electromagnet fixedly mounted to the handpiece of the surgical tool and a permanent magnet so mounted to the driving element that activation of the electromagnet urges the driving element to move longitudinally of the tool.

The driven element is preferably fixedly mounted to energy generation means of the surgical tool, optionally to an energy conversion means thereof.

The elongate member may then comprise an elongate energy transmission member mounted to the energy generation means, optionally to the energy conversion means thereof.

The energy generation means may comprise a source of ultrasonic vibrations, and the energy conversion means may then comprise an ultrasound amplification/conversion horn.

The driven element preferably comprises an integral portion of one of the energy generation means and the energy conversion means.

The driven element is advantageously joined to one of the energy generation means and the energy conversion means adjacent a nodal plane of oscillations therein.

The oscillations may comprise ultrasonic vibrations.

Preferably, the surgical tool of any of the above embodiments is provided with a detector to detect a rotational position of the elongate member and the effector.

Advantageously, the detector to detect a rotational position comprises a potentiometer arrangement, whereby a rotational position is converted to an electrical signal.

Preferably, the surgical tool comprises a controller to govern the rotational movement of the elongate member and the effector.

The controller to govern the rotational movement of the elongate member and the effector may comprise the detector to detect a rotational position thereof.

The controller to govern rotational movement may be adapted to select a rotational velocity of the elongate member and the effector based on a current rotational position thereof and a target rotational position input by a user, optionally on a continuous basis.

The controller to govern rotational movement may regulate a supply of power to the rotation mechanism in order to produce a selected rotational velocity, optionally by means of a pulse width modulated signal.

According to a second aspect of the present invention, there is provided a handpiece for a surgical tool comprising a manipulable handpiece member mountable to a proximal end of an elongate member having adjacent its distal end an effector defining a plane of operation, and a rotation mechanism adapted controllably to rotate such an elongate member and effector together about a longitudinal axis of the elongate member so as to align said plane of operation of the effector in a desired orientation.

BRIEF DESCRIPTION OF THE DRAWING FIGURES

Embodiments of the present invention will now be more particularly described by way of example and with reference to the accompanying drawings, in which:

FIG. 1b is a cross-sectional plan view of the handpiece of FIG. 1a, showing acoustic elements;

FIG. 1c is a cross-sectional side elevation of the handpiece of FIG. 1a, showing the acoustic elements;

FIG. 1d shows vibrational displacement characteristics of the acoustic elements shown in FIGS. 1b and 1c;

FIG. 2 is a side elevation of the handpiece shown in FIG. 1a;

DETAILED DESCRIPTION

Figure 1A:
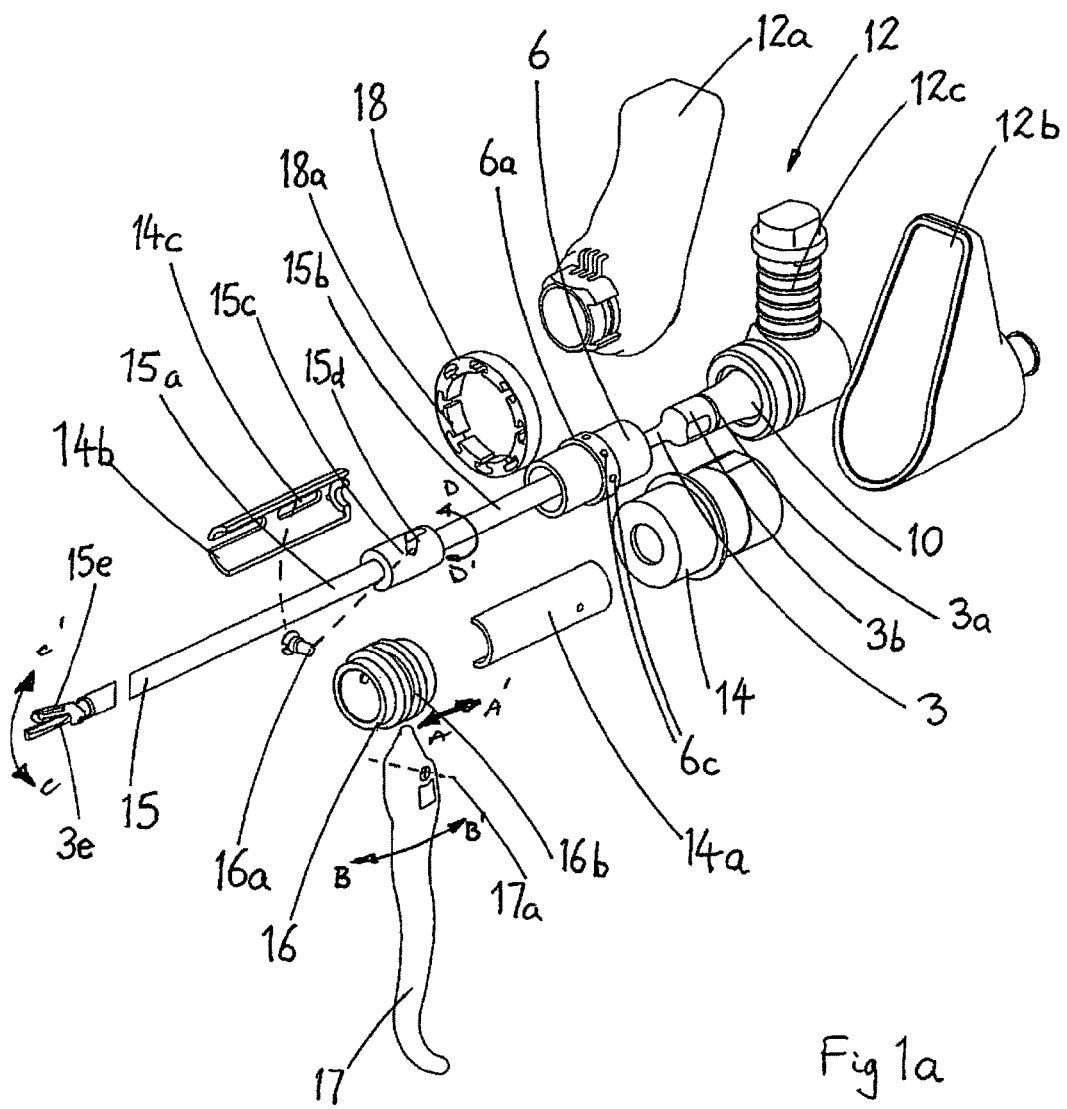
FIG. 1a shows, schematically, an exploded perspective view of components of a first handpiece of an ultrasonically-activatable surgical tool embodying the present invention, including cross sections of juxtaposed elements of its acoustic system.

Referring now to the Figures and to FIG. 1a in particular, an acoustic system for an ultrasonically-actuable surgical tool comprises a transducer 12, a waveguide 3 operatively connected thereto, and a distal end effector 3e. An isolating sleeve 6 is mounted to the acoustic system within a handpiece casing 1 (for which, see FIG. 2). The acoustic system is mounted within casing components 12a and 12b. Coupling sleeve 14 and its extension components 14a and 14b is attached to an inner tube 15b of a contra rotatable tube-set 15 extending coaxially around the waveguide 3. The tube-set 15 comprises said inner tube 15b, an outer tube 15a and an outer tube collar 15c; a helical slot 15d extends around the outer tube collar 15c.

The outer tube collar 15c is either integral with, or mouldably attached to, said outer tube 15a, so as to cause pivoting movement of a distally-mounted hinged jaw 15e in the direction of arrows C and $C^1$ when the outer tube collar 15c is reciprocally rotated in the direction indicated by arrows D and $D^1$. (A variety of mechanisms to convert rotational movement of the outer tube 15a to pivoting movement of the jaw 15e are known from the above references and elsewhere.) The outer tube collar 15c is urged to rotate by a slide ring 16 provided with a drive pin 16a which engages with said helical groove 15d of the outer tube collar 15c through an axial slot 14c in extension component 14b. This slide ring 16 is in turn moved longitudinally in the direction of arrows A and $A^1$ by manual movement of a trigger 17 pivotally mounted about axis 17a and engaged at its inner tip with a circumferential groove 16b extending around the slide ring 16. Manual movement of the trigger 17 thus causes corresponding rotation of jaw 15e according to arrows C and $C^1$. The plane defined by the end-effector 3e and the travel of the jaw 15e comprises a cutting plane of the tool.

The rotation of the acoustic system and attached isolating elements, 6, 14, 14a, and 14b, relative to the handpiece casing 1, about the longitudinal axis of said acoustic system, may be achieved by several exemplary means.

An advantageous embodiment is shown schematically in FIGS. 1a to 1c. The acoustic system, comprising the transducer 12, the waveguide 3, and its end effector 3e, together with the jaw 15e adjacent to the end effector 3e and pivotable into engagement therewith, has the integrally or clamped compressively coupled isolating sleeve 6 positioned between an ultrasonic horn 10 and a proximal section 3b of the waveguide 3, at an annular interface 3a. The isolating sleeve 6 has a vibrational displacement node 6d (see FIG. 1d) located at a distance from interface 3a corresponding to one quarter of a wavelength of ultrasonic vibrations therein.

A circumferential flange 6a is integral with the isolating sleeve 6 and co-incidental with nodal plane 6d, said flange 6a containing a plurality of "hard" permanent magnets 6c inserted radially and at regular circumferential intervals around the flange 6a. Said magnets may be made of NdFeB or other suitable magnet material.

As shown in FIG. 1a, a "soft" magnetic stator core 18 comprises a plurality of electromagnet elements 18a, disposed coaxially around the flange 6a, with a radial gap 18b between them. The stator core 18 is firmly held stationary within the handpiece casing 1. An even number of permanent magnets 6c inserted into the flange 6a is matched by an equal number of electromagnetic elements 18a in the fixed stator ring 18. Electromagnet windings are coiled around each electromagnet element 18a, and may controllably be supplied with direct current through the housing 12a, 12b of the transducer 12, coupled via a cable 30 to a generator or other DC source 31 (see FIG. 1c).

Said electromagnet windings are connected in radially opposed pairs so as to provide alternating magnetic polarity between adjacent windings when current is passed therethrough, causing a magnetic interaction with the permanent magnets 6c in the nodal flange 6a. Pulsed activation of selected electromagnet winding coils is produced by control circuitry in the electrical generator 31. This activation is supplied in response to pressure on one or other of two switches 26a and 26b of a switch unit 26 conveniently mounted to an exterior of the handpiece 1 for fingertip access (see FIG. 2). Respective switches 26a, 26b reverse the direction of rotation of the acoustic system and functionally associated components.

In a preferred variation of this embodiment, the relative positions of the permanent magnets 6c, and of the stator core 18 and its electromagnetic elements 18a are reversed. Thus a ring of permanent magnets 6c would be mounted to the (static) handpiece 1 casing 12a, encircling a ring of electromagnet elements 18a arranged around the flange 6a on the (rotatable) isolating sleeve 6. When the windings around each electromagnet element 18a are energised, this arrangement works in the same way as that described above. A benefit of this preferred arrangement is that the handpiece 1 casing 12a, 12b is usually disposable (since it cannot be sterilised by autoclaving), and so it is preferable to mount the simple, cheap permanent magnets 6c to this component of the tool, and to mount the more complex electromagnet elements 18a to the autoclavable acoustic system.

The principle described above in respect of the embodiment shown in FIGS. 1a to 1c may be implemented as described by deploying a circumferential array of permanent magnets 6c around electromagnet elements 18a. Alternatively, a configuration based on that disclosed in U.S. Pat. No. 4,841,189 may be employed. The configuration of U.S. Pat. No. 4,841,189 comprises annular pole pieces having interleaved individually formed poles and permanent magnet rotor, but in the present invention may be transposed so that the electromagnet structures (hitherto described as the stator winding) is arranged to rotate within an array of permanent magnets mounted around its periphery.

Figure 5:
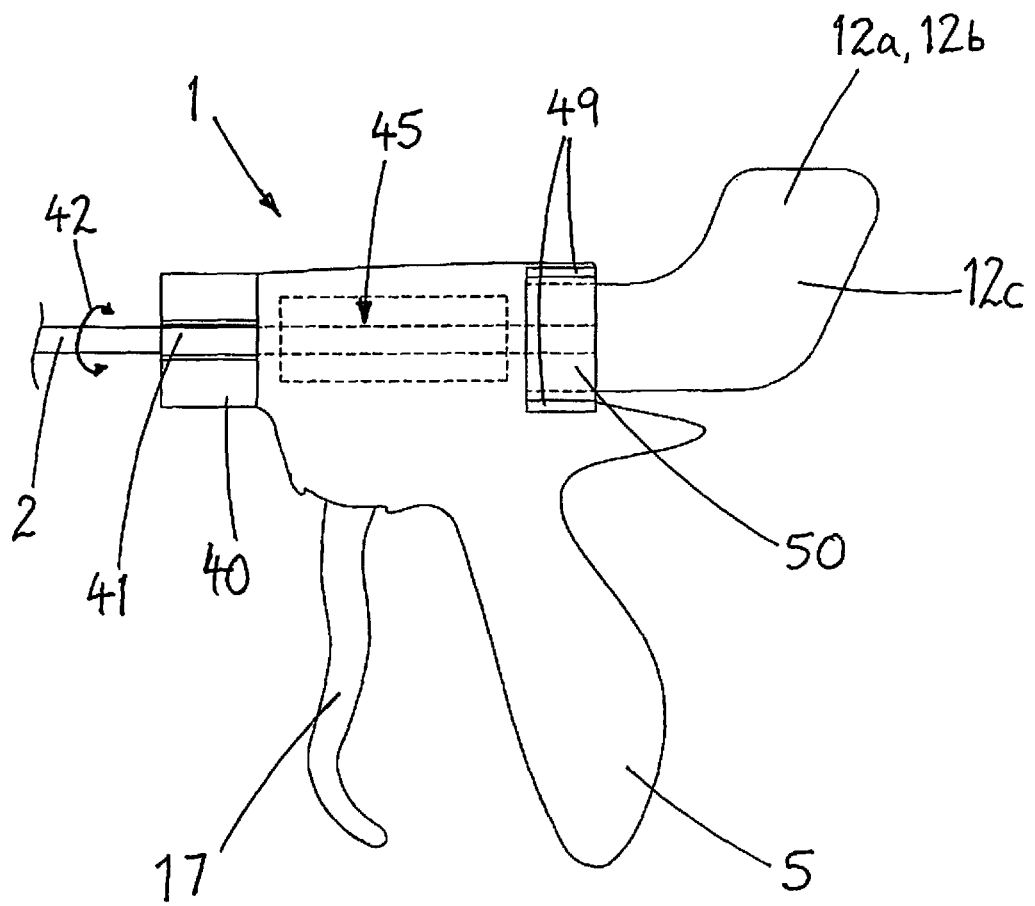
FIG. 5 is a schematic cross-sectional side elevation of a fourth handpiece of an ultrasonically-activatable surgical tool embodying the present invention.

Furthermore, any of the above structures may be mounted at different locations within a surgical instrument, in order to effect the required rotation, as will be described below and shown in FIG. 5. In this fourth embodiment, a distal portion of the drive assembly of the handpiece of the tool comprises fixed stator windings 40, mounted to a manually-graspable handle 5 of the tool, while magnetic rotor elements 41 are attached to a distally-extending handpiece member 2 (which may comprise the waveguide 3 or an equivalent energy transmission member) and a proximally-extending transducer 12 through a connecting mechanism 45. The member 2, the magnetic rotor elements 41, the connecting mechanism 45 and the transducer 12 may thus be rotated about a longitudinal axis in the sense of arrow 42, relative to the handle 5 and a remainder of the casing 1 of the handpiece.

Alternatively, electromagnetic elements 50 may be incorporated into the casing 12a, 12b of the transducer 12, and are capable of generating a rotational torque by magnetic interaction with a permanent magnet array 49 fixed within the casing 1 of the handpiece, which is held by the handle 5 by a surgeon or other user.

This particular electromagnetic mechanism may be applied to any such tool or instrument requiring an electrical coupling to a power source/controller (such as generator 31 in FIG. 1c). This would include electrosurgical devices in which the ultrasonic components described herein would be substituted with electrodes carrying controlled electrical currents to an end-effector at the distal operative tip of the tool for tissue treatment.

Figure 3A:
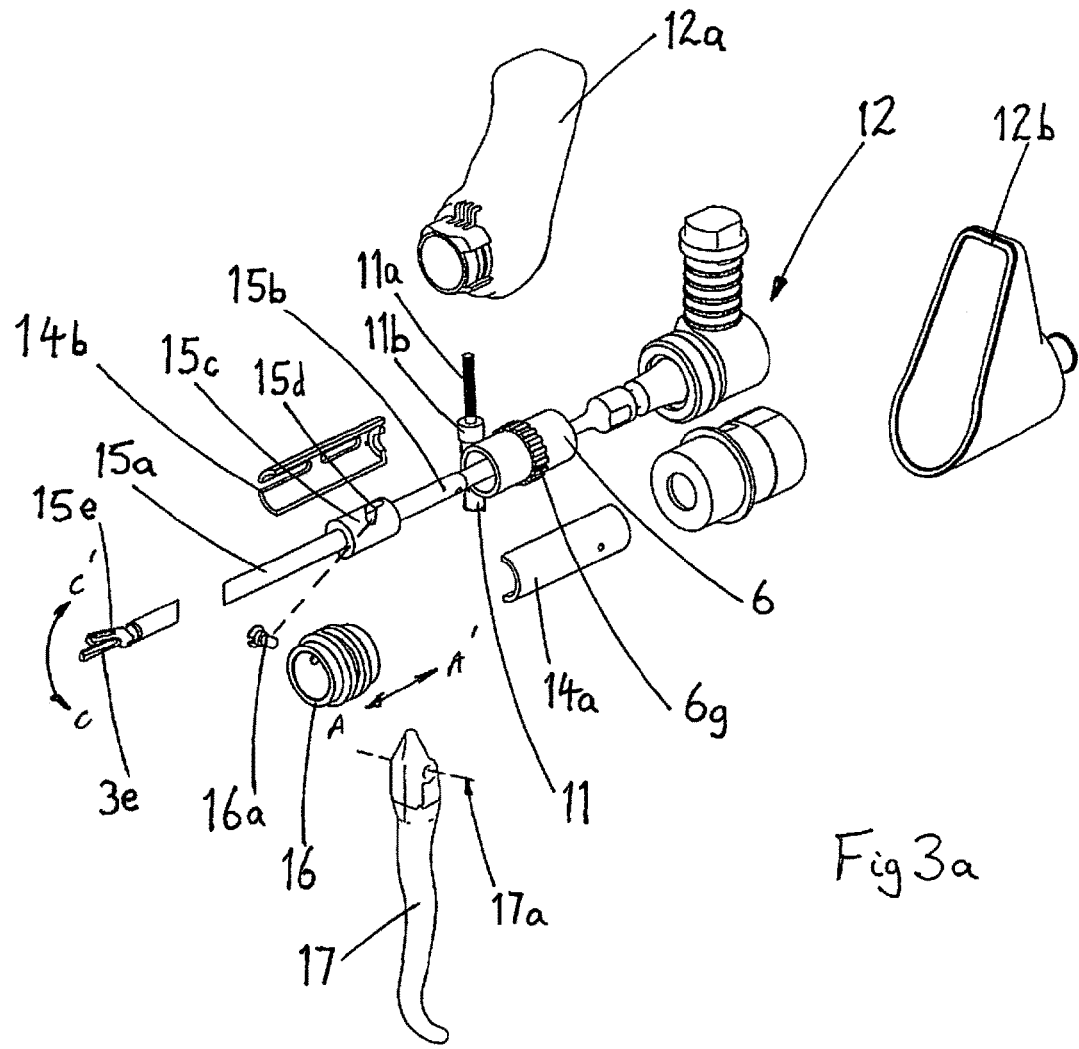
FIG. 3a shows, schematically, an exploded perspective view of components of a second handpiece of an ultrasonically-activatable surgical tool embodying the present invention, including cross sections of juxtaposed elements of its acoustic system.
Figure 3B:
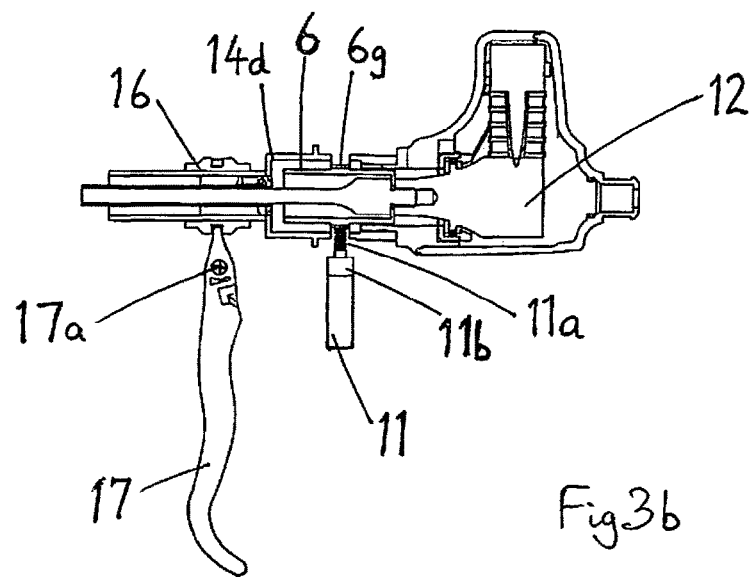
FIG. 3b is a cross-sectional side elevation of the handpiece of FIG. 3a, showing the acoustic elements.

An alternative means of rotation of the cutting plane of the tool may be effected by the second embodiment illustrated in FIGS. 3a and 3b. The aforementioned isolating sleeve 6, with its same nodal plane 6d, is provided with a raised circumferential flange having a profile comprising a gear ring 6g. A tangentially-mounted electric motor 11, fixed to handpiece casing 1 has a gearbox 11b operatively connected thereto, provided with an output worm gear 11a, which is operatively engaged with said gear ring 6g. The motor 11 is activated by switches 26a and 26b on the exterior of the handpiece casing 1 and conveniently positioned for digital access.

In the tools illustrated, which contain 'L-shaped' transducers 12 adapted to produce torsional mode ultrasonic vibrations, rotation of the cutting plane would be limited to ±90° about a neutral plane. If an alternative axisymmetric transducer 12 were used, both the above approach and that described in the context of FIGS. 1a to 1c would be capable of 360° rotation of the cutting plane.

Figure 4A:
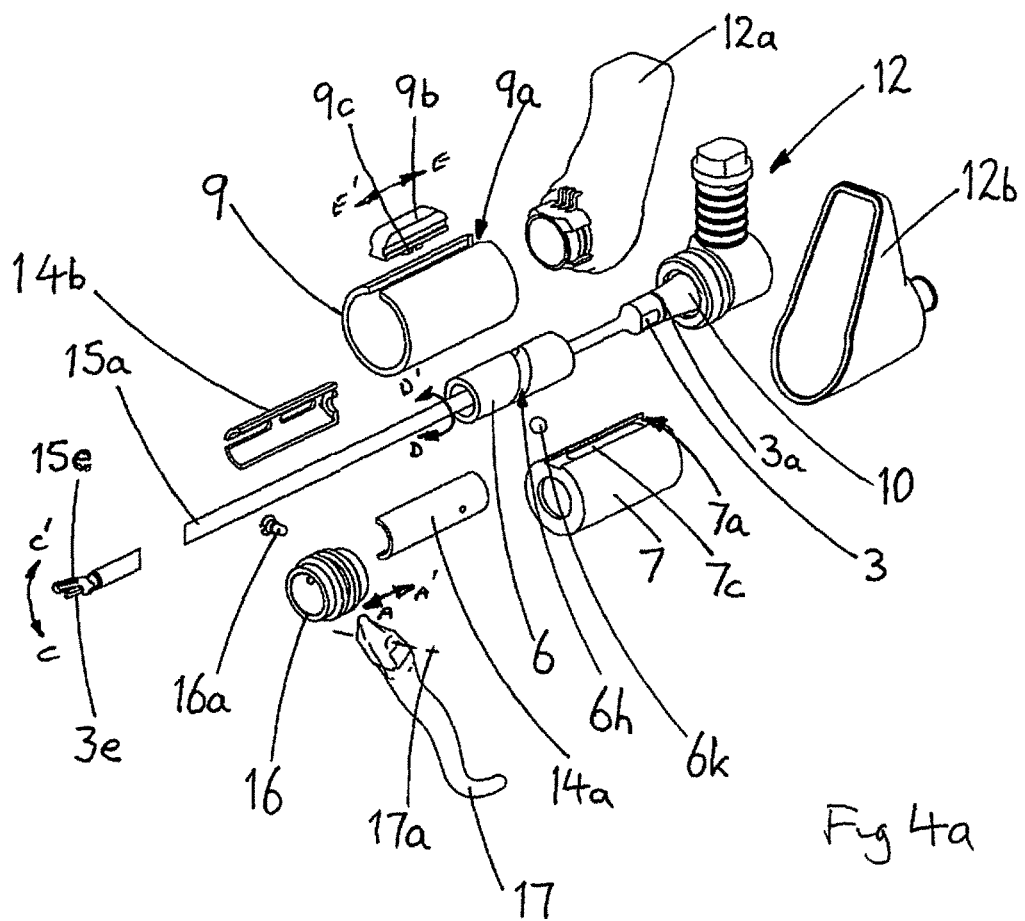
FIG. 4a shows, schematically, an exploded perspective view of components of a third handpiece of an ultrasonically-activatable surgical tool embodying the present invention, including cross sections of juxtaposed elements of its acoustic system.
Figure 4B:
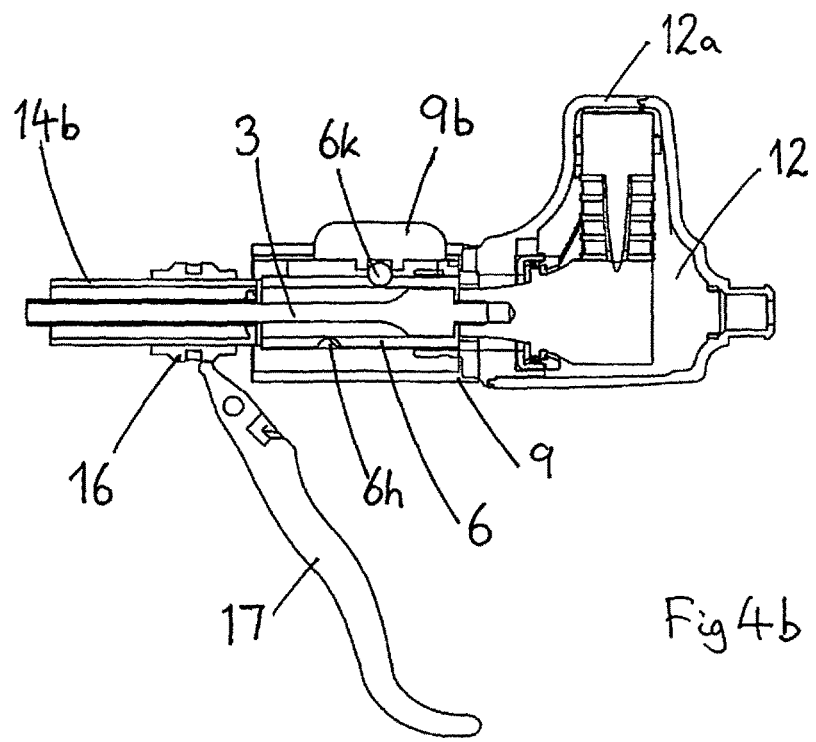
FIG. 4b is a cross-sectional side elevation of the handpiece of FIG. 4a, showing the acoustic elements.

A third embodiment of an arrangement for rotating the cutting plane is shown in FIGS. 4a and 4b. The acoustic isolating sleeve 6 is provided with a helically-extending slot 6h, within which is held a hardened ball 6k (see FIG. 4a). The ball 6k is compelled to move in a direction parallel to the longitudinal axis of the waveguide 3 by slideable knob 9b, which is constrained to travel within a longitudinal slot 9a in an outer sleeve 9. Slideable knob 9b is provided with a protruding socket 9c, which receives part of the ball 6k and which also passes through a longitudinal slot 7c in an inner slide sleeve 7. Longitudinal movement of the knob 9b, in the direction of arrows E and $E^1$, thus causes a corresponding rotational displacement of said acoustic isolator 6, and hence the transducer 12 and waveguide 3 connected thereto, as indicated by arrows D and $D^1$. The inner slide sleeve 7 is operatively connected at its distal end to tube holder 14, and at its proximal end to the transducer casing 12a, in order to achieve effective positional movement of all the components which control the orientation of the cutting plane.

Figure 6:
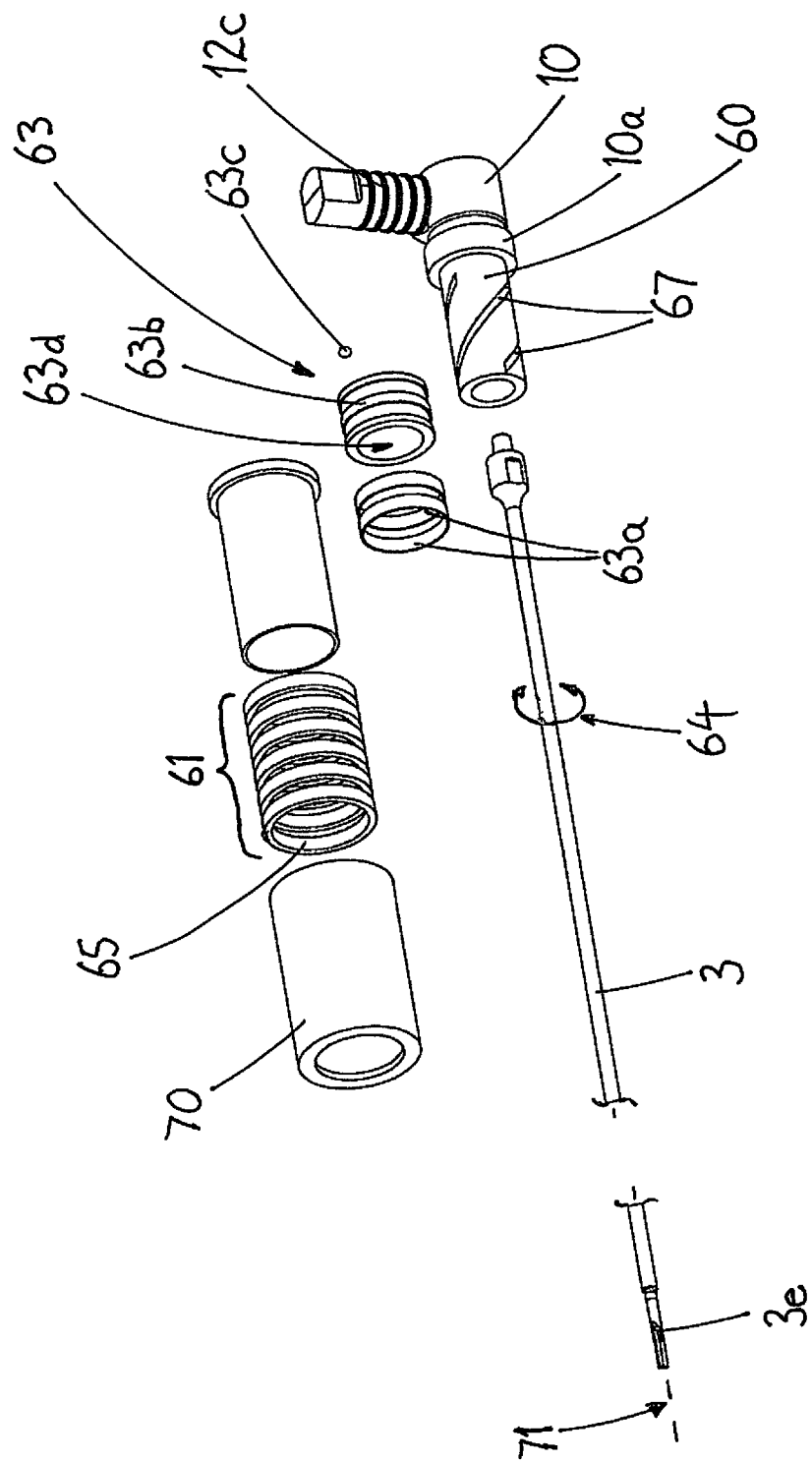
FIG. 6 is shows, schematically, an exploded perspective view of components of a fifth handpiece of an ultrasonically-activatable surgical tool embodying the present invention.
Figure 7:
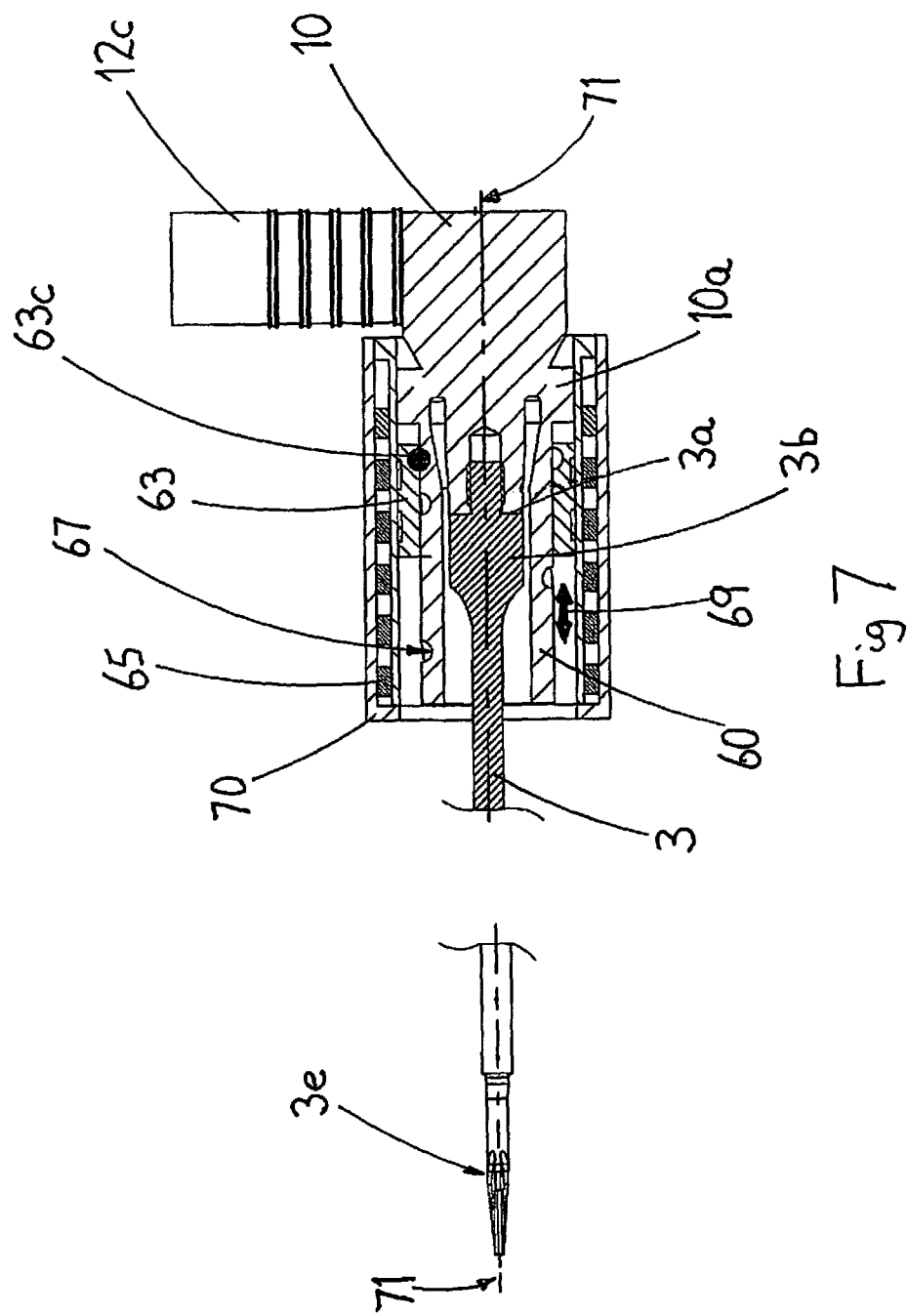
FIG. 7 is a cross-sectional side elevation of the assembled handpiece components of FIG. 6.

A fifth embodiment of an arrangement for rotating the cutting plane is shown in FIGS. 6 and 7. This arrangement is believed to be particularly effective, both in the magnetically-driven variant described in detail below and in a pneumatically-driven variant, which is described in outline only.

The arrangement of FIGS. 6 and 7 employs a linear magnetic drive, the longitudinally movable component of which is coupled to a cylindrical sleeve comprising part of the acoustic horn of the ultrasound generation/conversion system. A ball, pin or the like is held by the movable component of the linear magnetic drive and travels within a helical groove extending around an outer surface of the cylindrical sleeve, such that longitudinal motion of the linear magnetic drive causes rotational motion of the cylindrical sleeve and the acoustic horn of which it forms part. A conventional elongate waveguide is mounted to the acoustic horn, such that the entire acoustically-vibratable assembly rotates about its longitudinal axis, rotating the cutting plane of the end effector located at a distal end of the waveguide.

Looking at this embodiment in more detail, with reference to FIGS. 6 and 7, a transducer stack 12c is eccentrically mounted to an ultrasound conversion/amplification horn ("ultrasonic horn") 10. An elongate waveguide 3 is mounted coaxially extending from the ultrasonic horn 10 and has adjacent its remote distal end an end effector 3e. The end effector 3e may comprise a cutting edge defining a surgical plane, or may comprise part of a jaw mechanism as shown in FIG. 1, co-operating with a pivotable jaw 15e. The end effector 3e and jaw 15e would then define the surgical plane between them. The waveguide 3 and ultrasonic horn 10 between them define a longitudinal axis 71 of the surgical tool.

A hollow cylindrical sleeve element 60 extends distally from the horn 10, coaxially enclosing a proximal end 3b of the waveguide 3 and the annular interface 3a between the horn 10 and the waveguide 3, across which ultrasonic vibrations are transmitted to the waveguide 3.

An annular flange 10a extends outwardly from the horn 10 adjacent the junction of the horn 10 and a proximal end of the cylindrical sleeve element 60. The annular flange 10a and the junction of the sleeve element 60 are located at or closely adjacent to a nodal plane 10a of the ultrasonic vibrations in the horn 10, and so the annular flange 10a and the sleeve element 60 are isolated from said vibrations. Ideally, the annular flange 10a and the sleeve element 60 are formed integrally with the horn 10.

One or more helical grooves 67 extend around an outer face of the cylindrical sleeve element 60. These helical grooves 67 extend almost from end to end of the cylindrical sleeve element 60, but are closed at each end.

A hollow cylindrical drive member 63 coaxially encircles the cylindrical sleeve element 60, and is free to slide longitudinally along the outer surface of the cylindrical sleeve element 60. The drive member 63 holds one or more low-friction balls 63c in respective recesses on its internal cylindrical surface 63d, such that the or each ball 63c is also received engagingly in a respective helical groove 67 on the outer cylindrical surface of the cylindrical sleeve element 60 of the horn 10. The ball or balls 63c thus operatively connect the drive member 63 and the cylindrical sleeve element 60.

The cylindrical drive member 63 is provided with two or more annular permanent magnet rings 63a coaxially encircling its outer surface, the permanent magnet rings 63a being spaced apart by soft magnetic rings 63b.

The permanent magnet rings 63a preferably comprise a magnetic composition containing neodymium, or a similar rare earth composition.

The cylindrical drive member 63 is in turn coaxially encircled by a phased array of electromagnetic coils 65; an even number of said coils 65 is preferred. When the phased array of coils 65 is energised by passage of electrical current therethrough, the array 65 interacts with the permanent and soft magnet rings 63a, 63b on the drive member 63 to form a linear magnetic drive. The drive member 63 can thus be controllably driven back and forth, longitudinally of the array 65 and of the sleeve element 10, as shown by arrows 69.

This longitudinal motion of the drive member 63 causes the sleeve element 10 to move, being engaged by means of the balls 63c travelling in the helical grooves 67. The sleeve element 10 thus rotates about the longitudinal axis 71 of the tool. As a result, the entire ultrasonic horn 10, together with the transducer stack 12c and the waveguide 3, is driven to rotate about the longitudinal axis 71. This in turn rotates the surgical plane of the end effector 3e located at the distal end of the waveguide 3.

The array of electromagnetic coils 65 is held in a casing 70, which is fixedly mounted to a casing (not shown in FIGS. 6 and 7) of the handpiece. The casing 70 contacts the drive member 63 and the annular flange 10a of the horn 10 sufficiently closely to maintain the respective coaxial alignment of the various components, while allowing the drive member 63 to slide freely, longitudinally, and the annular flange 10a (and the horn 10, transducer stack 12c, sleeve element 67 and waveguide 3) to rotate freely within the handpiece.

Figure 2:
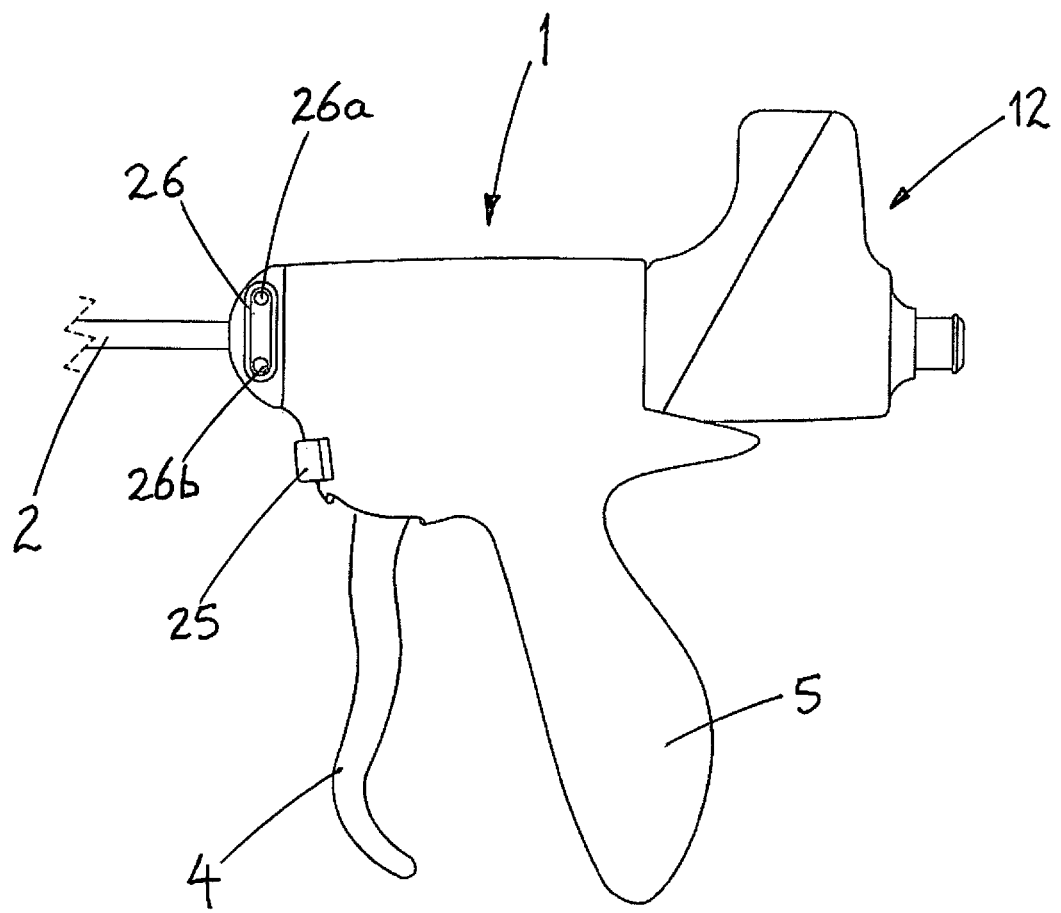

This arrangement produces smooth, controlled and continuous rotational movement of the surgical plane of the end-effector, activated by any desired form of control element (although fingertip controls 26, as shown in FIG. 2, should be particularly convenient to a user).

It is envisaged that the linear magnetic drive described above could be replaced by a pneumatic drive mechanism, the casing 70 representing an outer casing of a piston arrangement, and the drive member 63 the piston itself, driven to move longitudinally back and forth. The same arrangement of balls 63c in helical grooves 67 would be used to convert linear motion of the drive member 63 into rotational motion of the sleeve element 10a, horn 10 and so forth.

The generator 31, indicated schematically in FIG. 1c, has a primary function of controlling power delivery to the acoustic system, comprising the transducer 12, the waveguide 3, and its end effector 3e. The generator 31 may also incorporate circuitry designed to control cutting plane rotation and to regulate the timing of plane rotation in relation to acoustic activation.

Figure 8:
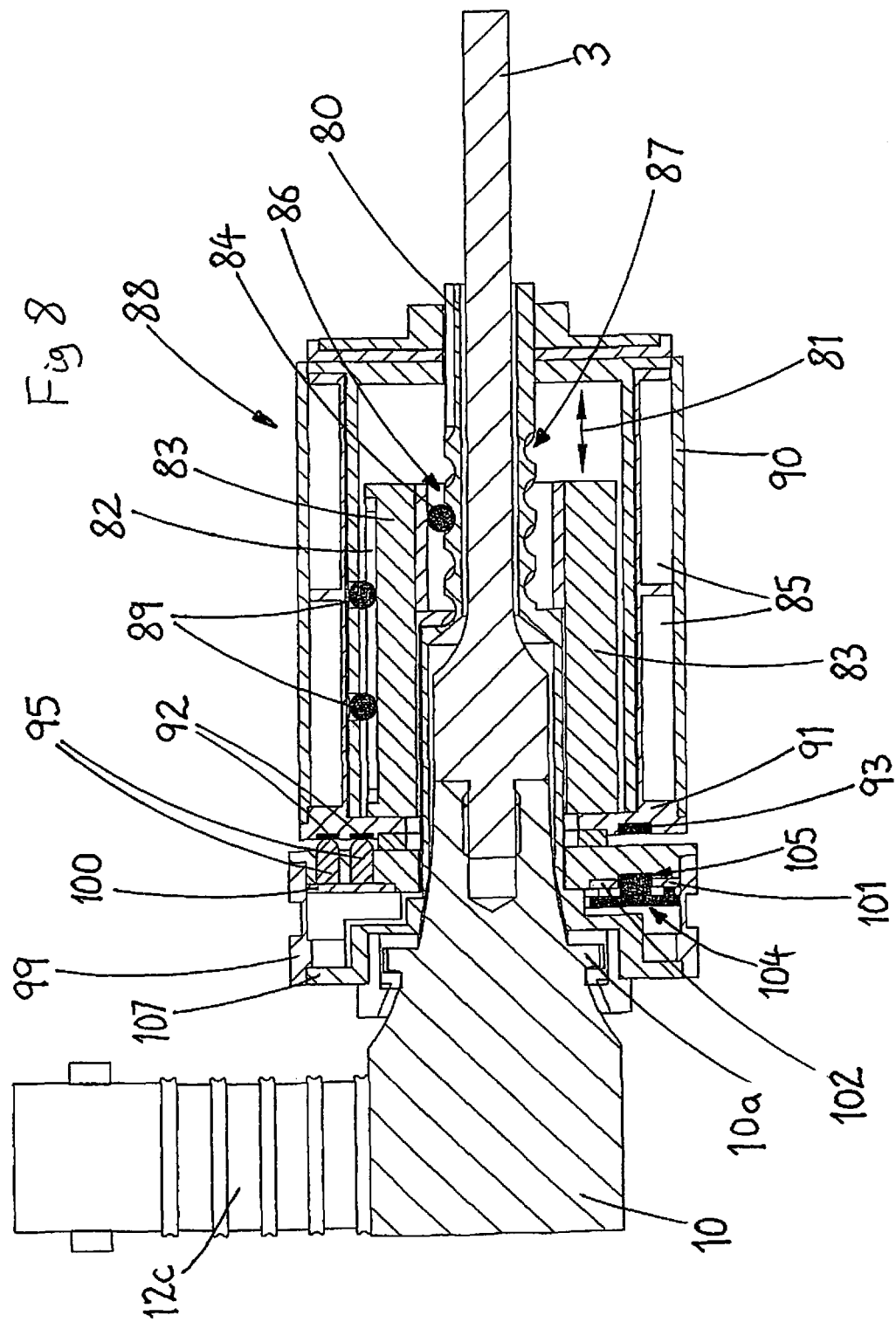
FIG. 8 is a cross-sectional side elevation of an operating mechanism of a sixth, preferred handpiece of an ultrasonically-activatable surgical tool embodying the present invention.
Figure 9:
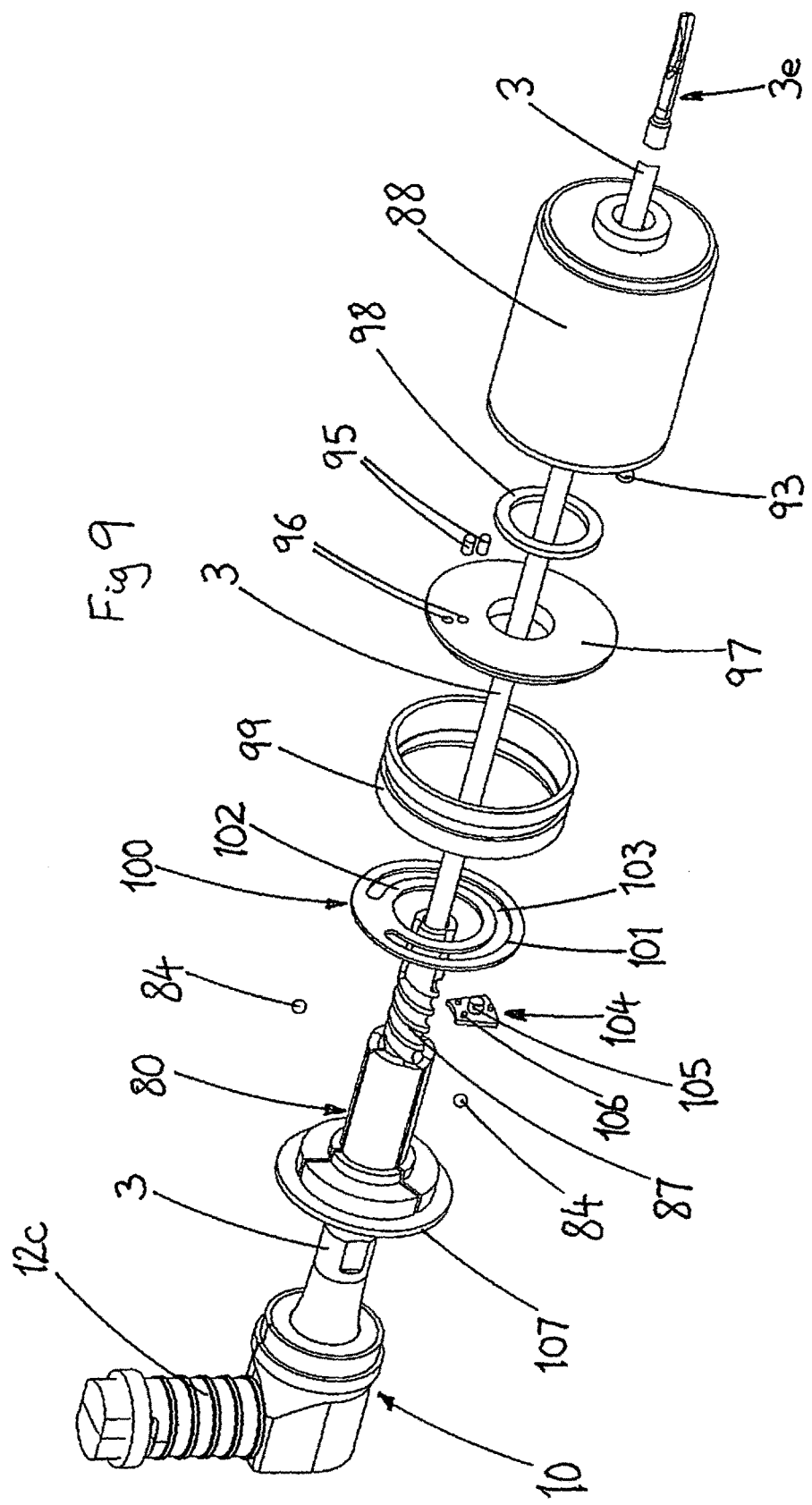
FIG. 9 is an exploded perspective view from a first direction of the operating mechanism shown in FIG. 8.
Figure 10:
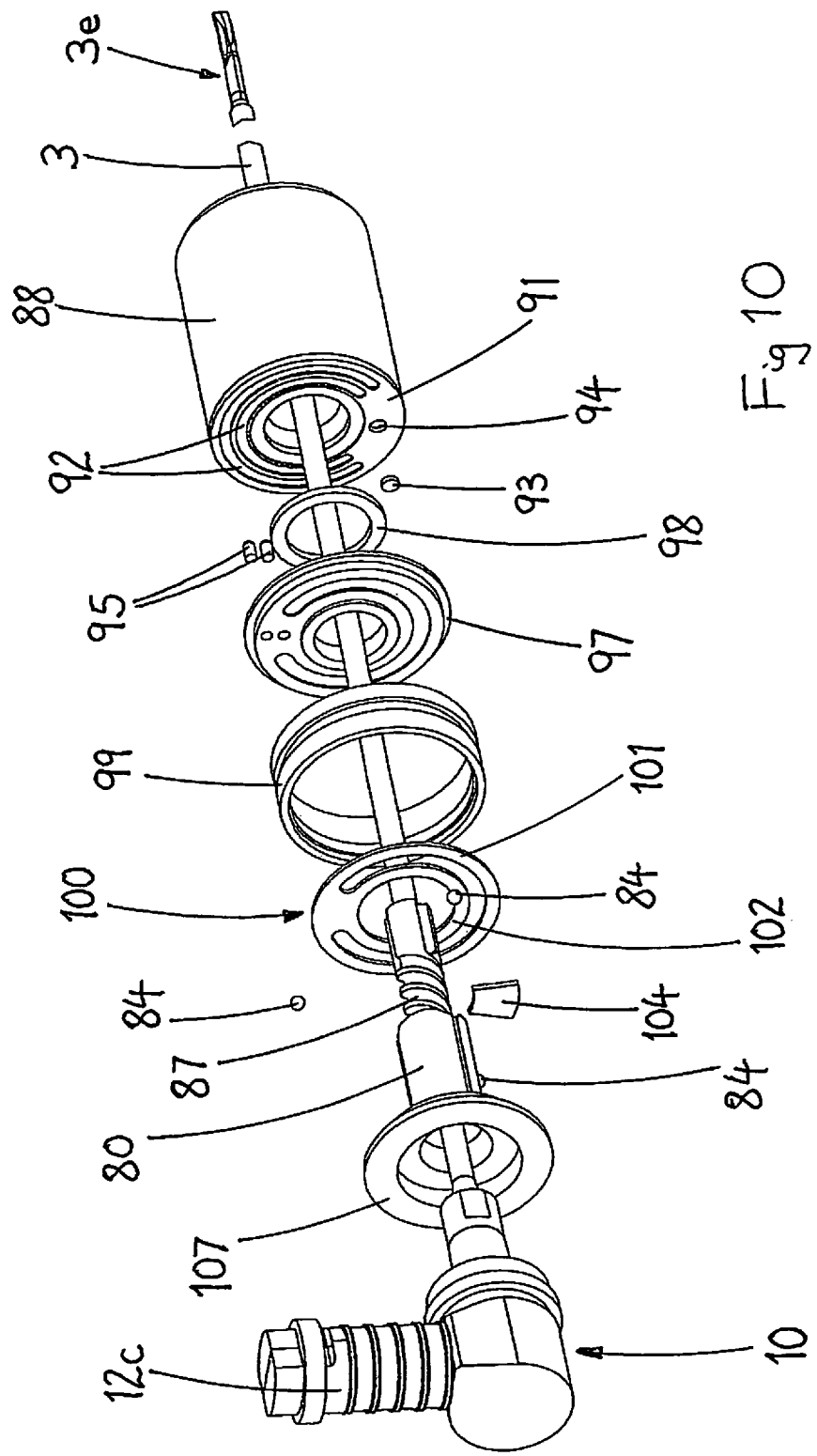
FIG. 10 is an exploded perspective view from a second direction of the operating mechanism shown in FIG. 8.

FIGS. 8 to 10 show a sixth, preferred embodiment of an arrangement for rotating the cutting plane. This is similar in principle to that shown in FIGS. 6 and 7, but also comprises a mechanism for detecting the current rotational position of the cutting plane and for producing a controlled and smooth rotational motion between positions of the cutting plane.

As in the fifth embodiment of FIGS. 6 and 7, this sixth embodiment employs a linear magnetic drive in conjunction with a helically-grooved transmission arrangement to convert the longitudinal motion of the linear magnetic drive to rotational motion of the stack, transducer, acoustic horn, waveguide and end effector.

The sixth embodiment also comprises a mechanism for detecting a current rotational position of these elements which employs a potentiometer mechanism to produce an electrical signal having a magnitude directly related to the rotational position. This signal is used as the basis for a control sequence (described in more detail below in respect of FIGS. 11a to 11d) for the drive that produces rapid, accurate, smooth and controlled motion between selected rotational positions.

A transducer stack 12c is mounted eccentrically to an ultrasound conversion/amplification horn ("ultrasonic horn") 10. An elongate waveguide 3 is mounted to extend coaxially from the ultrasonic horn 10, through a central axis of the drive mechanism 88, and has an end effector 3e at its distal end. This end effector 3e may comprise a cutting edge defining an operative plane. It may also comprise part of a jaw mechanism as shown in FIG. 1, cooperating with a pivotable jaw 15c, the operative plane being defined by the end effector 3e and the plane through which the jaw 15c is swept.

The drive mechanism 88 is centred around an elongate hollow cylindrical drive shaft 80, which is mounted at its proximal end to an annular flange 10a, extending radially outwardly from the ultrasonic horn 10 adjacent its junction with the waveguide 3. The annular flange 10a is located at or near a nodal plane in the ultrasonic vibrations set up in the horn 10 and waveguide 3, so as to isolate the drive mechanism from these vibrations.

Towards a distal end of the drive shaft 80, a set of three helical grooves 87 extend around its outer surface. The helical grooves 87 each have a part-circular cross-sectional profile to receive a respective one of three low-friction ceramic balls 84, which are thus free to travel along their respective helical grooves 87.

A hollow cylindrical permanent magnet 83 encircles the drive shaft. On its inner surface, a coaxial non-magnetic ring 86 (not shaded for clarity) holds the three ceramic balls 84 in respective part-spherical recesses, leaving the balls 84 free to rotate within each recess. The cylindrical permanent magnet 83 is free to travel longitudinally back and forth along the drive shaft 80 and waveguide 3, as shown by arrow 81.

The permanent magnet 83 has three straight grooves 82 extending longitudinally along its outer surface, spaced at 120° to each other around its circumference. These each receive a pair of additional low-friction ceramic balls 89. Each of the additional ceramic balls 89 is also held in a part-spherical recess in an inner surface of a coaxially extending cylindrical outer casing 90 of the drive mechanism 88.

The outer casing 90 acts as a former for a set of circumferential electromagnet coils 85, which thus encircle the permanent magnet 83. The electromagnetic coils 85 extend along substantially a whole length of the drive mechanism 88, such that the permanent magnet 83 is still encircled thereby at any point along its longitudinal motion 81.

This mechanism is preferably controlled using a two-button, forward/reverse arrangement, similar to that shown in FIG. 2. Thus, when the electromagnetic coils 85 are energised, the permanent magnet 83 will be driven distally or proximally within the drive mechanism 88, depending on the direction of the current within the coils 85. The ceramic balls 89 are constrained to travel only within the straight longitudinal grooves 82 on the outer surface of the permanent magnet 83, and so in turn constrain the permanent magnet 83 to purely longitudinal back and forth motion.

Meanwhile, the ceramic balls 84 bridge between the inner surface of the hollow cylindrical permanent magnet 83 and the helical grooves 87 on the drive shaft 80. Longitudinal motion of the permanent magnet 83 thus constrains the ceramic balls 84 to travel longitudinally, but since they are also constrained to travel within the helical grooves 87, the drive shaft 80 must therefore rotate to allow this, and with it the stack 12c, horn 10, waveguide 3 and effector 3e.

This structure effectively defines a gearing arrangement between the linear magnetic motor and the rotatable portion of the drive mechanism. Selection of a suitable "stroke length" for the movement of the permanent magnet 63, together with the number and pitch of the helical grooves 87, ensures that the effective gear ratio of this arrangement is sufficient to drive the rotatable portion to rotate without significant resistance, as well as ensuring that the full "stroke length" of the movement of the magnet 83 produces a sufficient rotation of the rotatable portion. A total rotational range of slightly less than a full circle is preferred, for constructional and control reasons. If necessary, the surgeon can supply the last few degrees of adjustment by hand movements, without significant inconvenience or fatigue.

The sixth embodiment also comprises a potentiometer sensor arrangement for determining the exact rotational position of the drive shaft stack, transducer, horn, waveguide and end effector. In essence, a conductive element is held stationary while bridging a conductive track and a resistive track, which rotate along with the waveguide, etc. An electrically conductive path is thus set up along the conductive track, across the stationary conductive element and back along the resistive track, and the resistance of this path depends on exactly where the conductive element bridges to the resistive track. Hence, a potential across this conductive path is directly related to the relative rotational positions of the tracks and the stationary conductive element.

One implementation of this approach is shown in FIGS. 8 to 10. The outer casing 90 of the drive mechanism 88 is fixed to the handpiece of the surgical tool (not shown) and thus does not rotate. An end plate 91 of the drive mechanism 88 is provided with a recess 94 which holds a permanent locating magnet 93 (the function of which is described below).

A low-friction bearing ring 98, made of PTFE (polytetrafluoroethylene) or the like, is located between the end plate 91 and a front plate 97 of the sensor arrangement, so that the sensor arrangement may rotate freely with respect to the drive mechanism 88. The sensor front plate 97 supports two spring loaded contact pins 95 in respective sockets 96, which contact two corresponding part-circular contact tracks 92 inset into the end plate 91 of the drive mechanism 88. This is a convenient arrangement for electrical power to be supplied to the electromagnet coils 85 of the drive mechanism 88. (The main power lead of such surgical tools generally leads to the transducer stack 12c, i.e. power is supplied to the rotatable components, so special contact arrangements are required for the coils of the drive mechanism which do not rotate).

A hollow cylindrical sensor housing 99 and a sensor back plate 107 (actually forming part of the proximal end of the drive shaft 80 in this example) cooperate with the sensor front plate 97 to enclose the sensor arrangement itself (in some embodiments, the interior of the sensor arrangement is filled with oil to reduce friction).

A generally annular printed circuit board 100 is almost completely divided into an outer annulus 101 and an inner annulus 102 by an almost-circular slot 103. The outer annulus 101 bears a circumferential resistive track, while the inner annulus 102 bears a corresponding circumferential conductive track around its surface.

A sliding contact 104 comprises a conductive flat plate with a permanent ferromagnet 105 extending from its centre, and several sprung contact pins 106 at its periphery. The permanent ferromagnet 105 extends through the slot 103 in the printed circuit board 100 and is strongly coupled to the permanent locating magnet 93 on the drive mechanism 88. This urges the contact pins 106 into contact with the respective tracks on the outer and inner annuli 101, 102 of the printed circuit board 100. When the printed circuit board 100 rotates with the sensor arrangement, this magnetic attraction holds the sliding contact 104 stationary, so it contacts the tracks at a different point. The sliding contact 104 thus provides the conductive bridge between the conductive and resistive tracks, required for the potentiometer arrangement referred to above.

The sensor back plate 107 carries a range of PCB tracks, electrical connections and so forth, connected to internal wiring, leading for example to the contact pins 95 and the drive mechanism 80, as well as to the printed circuit board 100 and other tool controls. This circuitry is of conventional form and so is not shown, for clarity.

In an alternative potentiometer arrangement (not shown), the sliding contact plate 104 is replaced by a magnetic conductive sphere. The resistive track still extends around an outer margin of the printed circuit board 100, but the conductive track extends around an adjacent portion of an inner surface of the sensor housing 99. The sphere is magnetically held in alignment with the permanent magnet 93 on the drive mechanism 88, which also holds it in contact with both tracks. The sphere thus remains stationary while the tracks and the sensor arrangement rotate, providing a conductive bridge for the conductive path of the potentiometer arrangement.

Both arrangements produce a simple voltage output that is accurately dependent on the current rotational position of the sensor arrangement, and hence of the other rotatable components of the surgical tool. This has been found to be superior to optical methods of identifying the rotational position (e.g. with a stationary photo-cell responding to black lines on an otherwise white rotating element). The optical arrangement only indicates when the rotation has already reached a desired point, for example, necessitating a crash stop to avoid an overshoot. The potentiometric arrangement allows the position to be tracked continuously, permitting far more effective and subtle control. Merely rotating between estimated positions by dead reckoning is far too inaccurate.

It should be noted that in each case, the surgical tool is set up for the rotatable elements to index between a relatively small number of pre-set rotational positions. This is much easier to control than a system allowing infinite variations of position, while the surgeon can easily adjust the angle of the tool by a few degrees if an indexed position is not quite ideal.

Figure 11A:
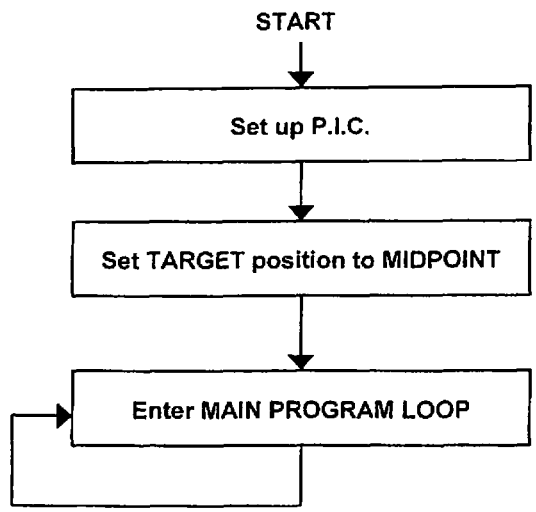
FIG. 11a to 11d are schematic flow charts of portions of a control method for the operating mechanism shown in FIG. 8.
Figure 11B:
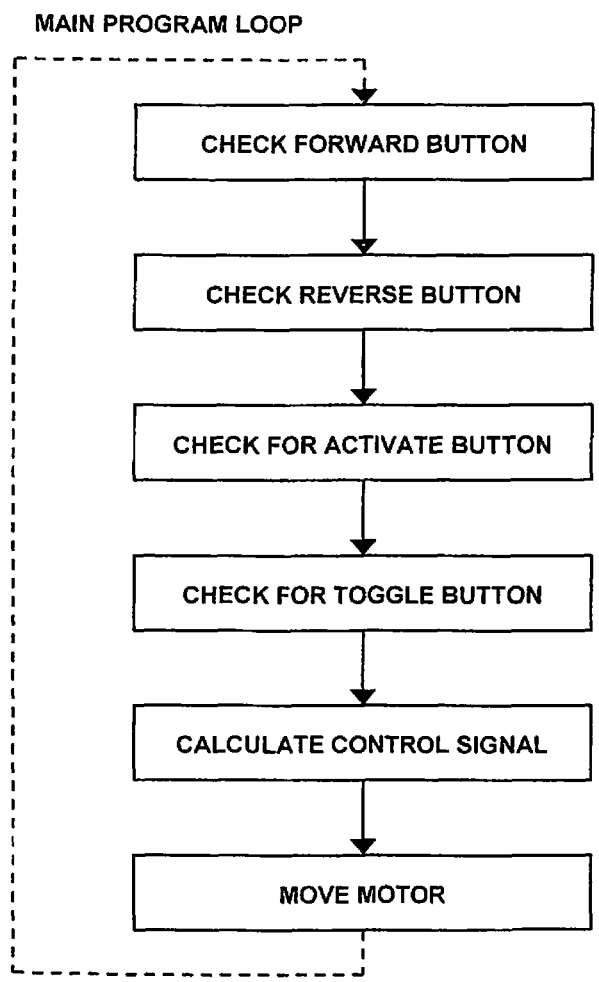
Figure 11C:
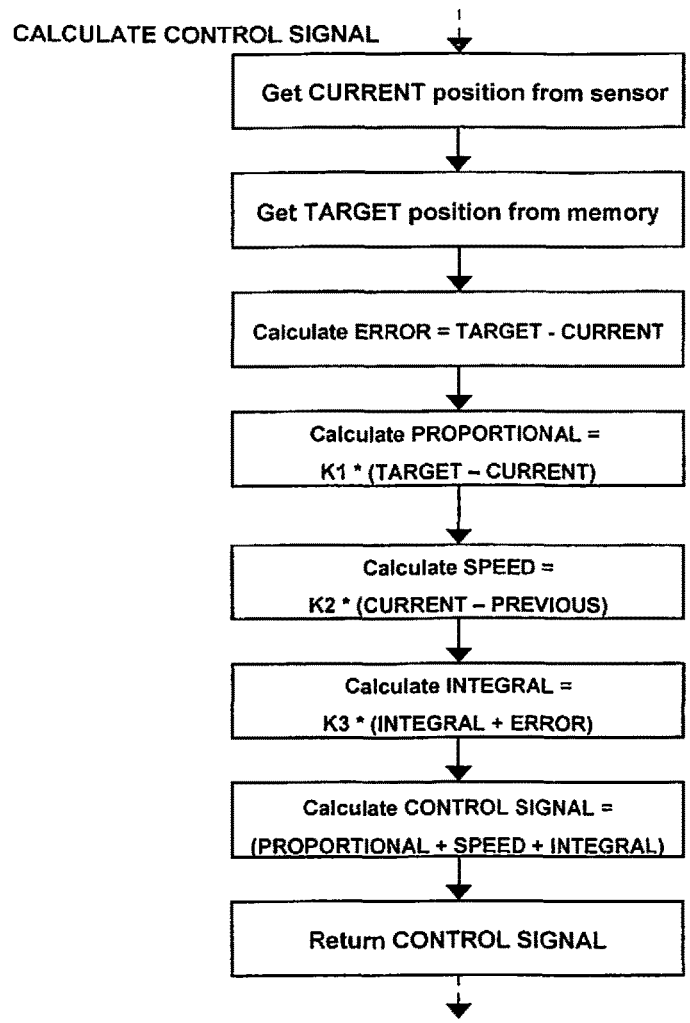

The control procedure for the rotation of the stack, horn, waveguide and end effector follows the sequence set out in FIGS. 11a to 11d. FIG. 11a shows the whole sequence of operation; FIG. 11b expands the structure of the MAIN PROGRAM LOOP from FIG. 11a; FIG. 11c expands the structure of the CALCULATE CONTROL SIGNAL step from FIG. 11b; and FIG. 11d expands the structure of the MOVE MOTOR step from FIG. 11b.

Referring to FIG. 11a, when the equipment is switched on, a PIC (Peripheral Interface Controller) chip is activated. This is conveniently located within a control unit for the ultrasound generator of the surgical tool. The PIC is set up, and variables described below are set to their default initial values.

In particular, the variable TARGET, indicating the desired rotational position of the surgical tool, is set to MIDPOINT, corresponding to the midpoint of the possible rotational travel range of the stack, transducer, horn, waveguide and end-effector assembly. Thus, a surgeon will always start with the surgical tool set at this midpoint position and able to rotate in either direction as required.

The sequence then comprises repeated passes around the MAIN PROGRAM LOOP until the surgeon has completed use of the surgical tool.

Referring to the expanded structure of the MAIN PROGRAM LOOP in FIG. 11b, the first step is to check the FORWARD button of the controls provided. If a signal has been received from operation of this button by the surgeon, the variable TARGET is incremented, indicating that the desired rotational position is forwards/clockwise from the current potential position.

The next step is to check the REVERSE button of the controls. If a signal has been received, the variable TARGET is decremented, indicating that the desired rotational position is backwards/anti-clockwise from the current rotational position.

The third step is to check the ACTIVATE button, which is to activate the ultrasound generator to energise the stack, transducer, horn, waveguide and end-effector. If the ACTIVATE button is being operated, a master PIC controller activates the ultrasound generator, and the FORWARD and REVERSE buttons of the controls are inhibited. It is undesirable for the end-effector to be turning during operation of the tool, particularly if it is grasping or otherwise targeting a specific element of body tissue. Accidental operation of the FORWARD and REVERSE buttons is thus prevented.

The fourth step is to check the TOGGLE button, which alters the intensity of the ultrasound generated between pre-set levels. Again, operation of the TOGGLE button causes the master PIC controller to alter the intensity, while the FORWARD and REVERSE buttons are inhibited to prevent accidental operation.

The fifth step, CALCULATE CONTROL SIGNAL, is at the heart of the sequence, and is shown in more detail as a series of sub-steps in FIG. 11c.

The rotational position detector/sensor arrangement of the surgical tool is interrogated in the first sub-step to give the variable CURRENT for the present instantaneous rotational position of the surgical tool.

In the second sub-step, the variable TARGET is retrieved from memory, including any increments or decrements resulting from the first two steps of the MAIN PROGRAM LOOP.

A set of further variables are then calculated. The variable ERROR, in the third sub-step, is set to the (vector) difference of the TARGET and CURRENT variables, indicating how far the surgical tool is from the desired rotational position.

The variable PROPORTIONAL, in the fourth sub-step, is set to the (vector) difference between the TARGET and CURRENT variables, multiplied by a pre-set constant, K1.

The variable SPEED, in the fifth sub-step, is set to the (vector) difference between the CURRENT variable and the PREVIOUS variable multiplied by a second pre-set constant, K2. (The PREVIOUS variable corresponds to the value of CURRENT from the previous pass around the MAIN PROGRAM LOOP).

The variable INTEGRAL, in the sixth sub-step, is set to the value of INTEGRAL from the previous pass around the MAIN PROGRAM LOOP, incremented or decremented by the value of ERROR, and then multiplied by a third pre-set constant, K3.

The seventh sub-step comprises the calculation of the CONTROL SIGNAL variable from the sum of the variables PROPORTIONAL, SPEED and INTEGRAL. The value of CONTROL SIGNAL (as described below) governs the speed and direction of rotation of the mechanism. There is a pre-set maximum value for CONTROL SIGNAL to prevent excessive speed of rotation.

In the eighth sub-step, the variable CONTROL SIGNAL is returned. The net sign of CONTROL SIGNAL indicates whether a FORWARD/clockwise rotation or a REVERSE/anti-clockwise rotation will be produced. The magnitude of CONTROL SIGNAL naturally indicates the amount of power sent to the mechanism. At this sub-step, the magnitude of CONTROL SIGNAL is compared to a pre-set minimum threshold value. If it is below this threshold value, CONTROL SIGNAL is instead set to zero. This prevents the sequence producing a series of small jittery correcting movements, particularly when sufficiently close to a desired TARGET rotational position as to make no practical difference to the surgeon.

Figure 11D:
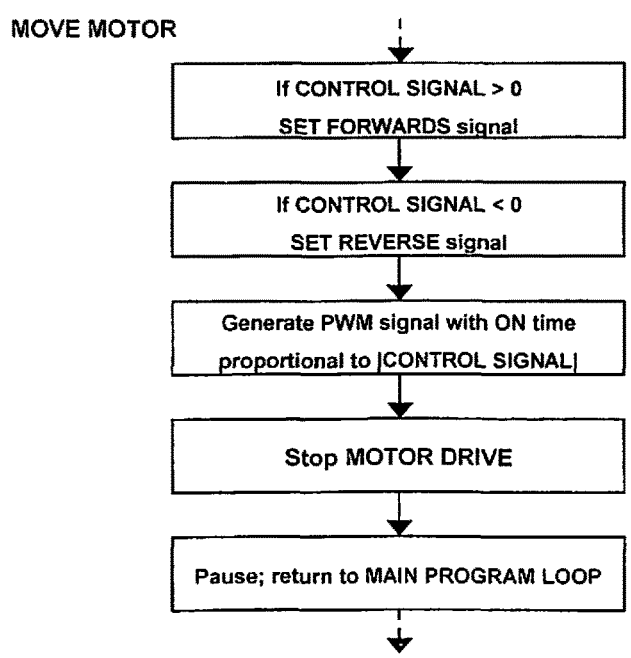

Control then transfers to the sixth step of the MAIN PROGRAM LOOP, which is set out in sub-steps in FIG. 11d.

In the first sub-step, if CONTROL SIGNAL is positive, the signal to the drive mechanism is set up to be in the FORWARDS/clockwise direction. In the second sub-step, if CONTROL SIGNAL is negative, this signal is set up to be in the REVERSE/anticlockwise direction. An asymmetric compensation coefficient may be used to adjust the FORWARD/REVERSE signals to ensure similar motion characteristics in both directions, should physical parameters of the equipment (e.g. an asymmetry in the resistance along the resistive track) cause them to differ.

In the third sub-step, the signal to the drive mechanism is generated as a PWM (pulse width modulated) current. The ON time of the PWM current is proportional to the magnitude of CONTROL SIGNAL. In the fourth sub-step, the drive mechanism, here indicated as MOTOR DRIVE, moves in response to the PWM current supplied. After a pre-set time interval, the MOTOR DRIVE is stopped and the control returns to the start of the MAIN PROGRAM LOOP. This loop will be followed, repeating the above steps and sub-steps, until the TARGET position is reached (or the position is sufficiently close that CONTROL SIGNAL is set to zero anyway).

The benefit of the above control sequence is to produce a smooth, controlled, accurate and proportionate rate of rotation of the mechanism. The rotation will be faster for larger position changes, but the rotation will gradually be slowed as the TARGET position is approached, coming to a controlled rest (rather than a jerky stop as soon as the system "realises" that it has arrived). Adjustment of constants K1, K2 and K3 should allow adjustment of the exact speed profiles produced, depending on the requirements of a particular tool, or even of a particular user.

Although the above examples are ultrasonically-vibratable surgical tools for minimally-invasive surgical techniques, the mechanisms shown for rotating an element of a tool about its axis should be applicable to a wide range of other surgical tools, and possibly even similar tools for non-surgical purposes. For example, tools are used in minimally-invasive surgery which employ directed RF (radio frequency) electric currents to cut or cauterise tissue; other tools used in minimally-invasive techniques comprise an elongate shaft with a tissue stapling attachment at the distal end. Both would benefit from mechanisms such as those described above. Such surgery is usually carried out under visualisation using a laparoscope, requiring the surgeon also to manipulate the laparoscope, in order to see clearly the exact point where he or she is operating. Smooth and controlled redirection of the viewing lens at the distal end of the laparoscope would be highly beneficial.

The invention claimed is:

1. A surgical tool adapted to be activated by ultrasonic vibrations comprising an elongate waveguide having a distal end and a proximal end, the elongate waveguide being provided adjacent said distal end with an effector defining a plane of operation and said elongate waveguide being adapted to transmit said ultrasonic vibrations to activate the effector, a manipulable handpiece disposed adjacent the proximal end of the elongate waveguide, and a rotation mechanism adapted to controllably rotate the elongate waveguide and the effector together about a longitudinal axis of the elongate waveguide so as to align said plane of operation of the effector in a desired orientation, wherein the rotation mechanism comprises at least two elements co-operably moveable relative to one another, comprising a longitudinally-displaceable driving element operatively engaged through helically-symmetrical engagement means with a rotatable driven element.

2. A surgical tool as claimed in claim 1, wherein the rotation mechanism comprises an electromagnetic drive mechanism.

3. A surgical tool as claimed in claim 1, wherein the rotation mechanism comprises a powered rotation mechanism provided with a hand-operable activation member.

4. A surgical tool as claimed in claim 3, wherein said hand-operable activation member is operable by a finger of a hand holding the handpiece.

5. A surgical tool as claimed in claim 4, wherein said hand-operable activation member is operable by finger-tip pressure.

6. A surgical tool as claimed in claim 3, wherein the rotation mechanism comprises a first hand-operable activation member and a second hand-operable activation member, operation of which respectively causes rotation in opposite directions.

7. A surgical tool as claimed in claim 1, also comprising a source of ultrasonic vibrations.

8. A surgical tool as claimed in claim 1, comprising an operating mechanism for the effector, said operating mechanism extending between the manipulable handpiece and the effector.

9. A surgical tool as claimed in claim 1, wherein the helically-symmetrical engagement means comprises a body protruding from a first of the driving and driven elements and received within a helically-extending groove of a second of the driving and driven elements.

10. A surgical tool as claimed in claim 1, further comprising a linear drive adapted controllably to displace the longitudinally-displaceable driving element.

11. A surgical tool as claimed in claim 10, wherein said linear drive comprises a linear electromagnetic motor.

12. A surgical tool as claimed in claim 11, wherein said linear electromagnetic motor comprises an electromagnet fixedly mounted to the manipulable handpiece of the surgical tool and a permanent magnet so mounted to the driving element that activation of the electromagnet urges the driving element to move longitudinally of the surgical tool.

13. A surgical tool as claimed in claim 1, wherein the rotation mechanism comprises a longitudinally manually displaceable first connecting element engaged with a helical second connecting element on a rotatable body.

14. A surgical tool as claimed in claim 1, wherein the rotation mechanism acts on an energy generation means or an energy conversion means of the surgical tool, to which said elongate waveguide is mounted.

15. A surgical tool as claimed in claim 1, wherein the surgical tool comprises a detector to detect a rotational position of the elongate waveguide and the effector.

16. A surgical tool as claimed in claim 15, wherein said detector to detect a rotational position of the elongate waveguide and the effector comprises a potentiometer arrangement producing an electrical signal proportional to said rotational position.

17. A surgical tool as claimed in claim 15, wherein the surgical tool comprises a controller to govern rotational movement of the elongate waveguide and the effector.

18. A surgical tool as claimed in claim 17, wherein the controller to govern the rotational movement of the elongate waveguide and the effector includes or is operatively connected to the detector to detect a rotational position of the elongate waveguide and the effector.

19. A surgical tool as claimed in claim 17, wherein said controller to govern rotational movement is adapted to regulate a rotational velocity of the elongate waveguide and the effector on the basis of at least a current rotational position of the elongate waveguide and the effector and a target rotational position selected by a user.

20. A surgical tool as claimed in claim 19, wherein said controller regulates said rotational velocity on a continuous basis.

21. A surgical tool as claimed in claim 17, wherein said controller to govern rotational movement provides power to the rotation mechanism by a pulse width modulated signal.

22. A surgical tool as claimed in claim 9, wherein said body protruding from the first of the driving and driven elements comprises a ball received within the helically-extending groove of the second of the driving and driven elements.

* * * * *